(12) United States Patent
Holzer

(10) Patent No.: US 6,683,065 B1
(45) Date of Patent: Jan. 27, 2004

(54) METHOD OF TREATING BODY INSECT INFESTATION

(75) Inventor: David Holzer, Miami Beach, FL (US)

(73) Assignee: Host Pharmaceuticals, LLC, Hillsdale, NJ (US)

( * ) Notice: Subject to any disclaimer, the term of this patent is extended or adjusted under 35 U.S.C. 154(b) by 0 days.

(21) Appl. No.: 09/937,627

(22) PCT Filed: Aug. 17, 2000

(86) PCT No.: PCT/US00/22577

§ 371 (c)(1),
(2), (4) Date: Sep. 27, 2001

(87) PCT Pub. No.: WO01/13954

PCT Pub. Date: Mar. 1, 2001

Related U.S. Application Data

(60) Provisional application No. 60/149,471, filed on Aug. 19, 1999.

(51) Int. Cl.⁷ .................... A61K 31/695; A01N 25/00
(52) U.S. Cl. ........................ 514/63; 424/405
(58) Field of Search ................ 424/405; 514/63

(56) References Cited

U.S. PATENT DOCUMENTS

| | | | |
|---|---|---|---|
| 4,146,619 A | * | 3/1979 | Lover et al. |
| 4,155,995 A | | 5/1979 | Heinz et al. |
| 5,045,536 A | | 9/1991 | Baker |
| 5,288,483 A | * | 2/1994 | Cardin et al. |
| 5,876,705 A | | 3/1999 | Uchiyama et al. |

FOREIGN PATENT DOCUMENTS

| | | |
|---|---|---|
| EP | 0 191 543 | 8/1986 |
| WO | WO 91/15953 | 10/1994 |
| WO | WO 01/19190 | 3/2001 |

* cited by examiner

*Primary Examiner*—Shengjun Wang
(74) *Attorney, Agent, or Firm*—Stroock & Stroock & Lavan LLP

(57) ABSTRACT

The present invention provides a method of treating lice and/or tick infestation, in both mature and immature forms, comprising topically applying a composition consisting of at least about 40% of polydimethylsiloxane by volume to the infestation and allowing the composition to remain on the infestation for at least 5 minutes, wherein the surface tension of the composition is below about 25 dynes/centimeter at 20° C. and the viscosity of the composition is above about 200 centistokes at 20° C.

6 Claims, No Drawings

METHOD OF TREATING BODY INSECT INFESTATION

This application is a 371 national stage filing of PCT/US00/22577, filed Aug. 17, 2000 which application claims benefit of U.S. Provisional Application Ser. No. 60/149,471, filed Aug. 19, 1999 the contents of which are herein incorporated by reference.

FIELD OF THE INVENTION

This invention relates to the safe and effective treatment of lice, nits (and other infestational insects) by using low surface tension lubricants.

BACKGROUND OF THE INVENTION

For centuries, people have been plagued by head lice, body lice, and pubic lice, which appear in numerous species all having similar physiological characteristics. Over the years, people have expended tremendous efforts and resources to develop a safe and effective method for eliminating the problem of lice and nits. To date, the only patented processes for killing lice and nits involve the use of poisons, pesticides or noxious soaps with numerous side effects and cautionary uses. These pediculicides. such as lindane, pyrethrum, or malathion, are not optimal for the treatment of lice or nits because they are not healthful, and because, over time, lice tend to develop a natural resistance to poison or pesticide formulation.

SUMMARY OF THE INVENTION

It is accordingly an object of the present invention to provide a method and chemical formulation for effective yet safe treatment for body insect infestation such as lice, fleas, and the like.

Generally present the invention compromises the direct treatment of body insect infestation with a synthetic lubricant, such as food grade silicon, to effectively kill infesting insects such as lice, and nits, as well as fleas, ticks and other insects. In Accordance with the present invention, the synthetic lubricant is applied directly to the insects, or is provided as a major (more than 50 volume percent) of a shampoo formulation. If added to a shampoo. the exact effective concentration level above 50% is determined based on both the nature of the synthetic lubricant, and the nature of the shampoo used.

DETAILED DESCRIPTION OF THE INVENTION

In order to illustrate the efficacy of the present invention the following test examples are presented.

EXAMPLE 1

Two tests were conducted using a compound containing 60% silicone-based oil. In the first test the compound was placed on a louse on a paper towel. After 5 minutes, the louse washed off with Prell® shampoo and water. The louse was observed one minute later and was dead. In the second test using the same compound, the compound was applied to the long, thick hair of a school girl, which had been infested with lice for several months. After five minutes, the compound was removed by several washes with Prell® shampoo, with the compound being otherwise difficult to extract from the hair. The infestation was successfully treated and no lice or nits returned.

EXAMPLE 2

Additional tests were conducted using a 100% concentration of Dow coming Fluid Food Grade silicone (350 CST) (the "silicone"). These tests also revealed that, in addition to killing lice, the silicone was effective at preventing nits from maturing. In these tests, silicone was applied directly to head lice, body lice and to the hair of several children infested with head lice.

In the first Silicone experiment, three head lice were collected from school children. The lice were placed on the hand of a subject and they attached themselves to the hair on the subject's hand. After five minutes, the lice were gently washed off with Prell® shampoo and then water.

Although there appeared to be mortality within minutes, the lice were left on the hand for further examination (they were covered with a loosely fitting bandage to make sure they did not fall off). During the following six hours, the lice were checked periodically and all were found to be dead.

EXAMPLE 3

In a further Silicone experiment, Silicone was directly applied to the hair of three school children, each of which had been infested with lice and nits. Each of the children applied the silicone directly to his or her hair and left it on for five minutes. After five minutes, the hair was washed first with Prell® shampoo and then with Johnson's Baby Shampoo®. In all three cases the infestation was successfully ended with one application.

In a continuing experiment, Silicone was directly applied to the hair of twenty school children, each of which had been infested with lice and nits. Each of the children applied the silicone directly to his or her hair and left it on for ten minutes minutes. After ten minutes, the hair was washed with a shampoo of the parent's choice. In all twenty cases the infestation was successfully ended with one application.

EXAMPLE 4

In another experiment ten adult lice were immersed in the Silicone for ten minutes, then washed and rinsed for one minute each in water. A set of ten control lice were immersed in water for ten minutes and then also washed and rinsed for one minute. The lice were then held in an incubator. A review of the lice after one hour, and again after twenty-four hours, revealed a 100% mortality of those who had been immersed in Silicone. There was no mortality among the controls.

EXAMPLE 5

In an additional experiment, ten adult lice were immersed in the Silicone for ten minutes, and subsequently washed in a dilution of 50:50 Johnson's Baby Shampoo® and tap water. To test the effectiveness at different concentrations of Silicone, four mixtures were made using the Silicone with Johnson's Baby Shampoo® with the following concentrations:

a. 100% Johnson's Baby Shampoo
b. 3% Silicone and 97% Johnson's Baby Shampoo
c. 15% Silicone and 85% Johnson's Baby Shampoo
d. 40% Silicone and 60% Johnson's Baby Shampoo
e. Control with water The results of the test after 24 hours were that for samples a and c, one louse was dead; for samples b and e, no lice were dead. The one louse being dead was considered not statistically significant. In sample d, containing 40% Silicone, four lice were dead, indicating that at this concentration there is some effectiveness of the Silicone in killing lice but not a fully useful concentration. It is believed that other ingredients may interfere with the effectiveness of the Silicone, and accordingly it is preferred to use the Silicone in a high concentration or in a pure state.

EXAMPLE 6

In another experiment to determine the effect of lubricants of various surface tensions, a test was done using 10 adult lice immersing them into one of three solutions for ten minutes and then washing them of with a soapy water solution. The three lubricants used were Johnson's baby oil a mineral oil, Ultra pure lamp oil 99% pure liquid paraffin, and Krytox® 1514 Vacuum pump fluid, produced by Dupont®. The lice were then observed after one hour, and three hours and the amount dead were the same at both intervals in all tests. The mortality rate was highest for the Krytox® 1514 with nine of ten dead within one hour, lowest for the liquid paraffin with three of ten dead within one hour, and moderate for the mineral oil with four of ten dead within one hour. In a repeat of the experiment for the Krytox, seven out of ten where dead within one hour, for liquid paraffin two out of ten, and for mineral oil five out of ten.

The preferred embodiment for use as a head lice treatment is to use the Silicone in its pure state, that is Dow Coming 200 fluid, 350 CST. Which is a silicone fluid termed Dimethyl polysiloxane. The Silicone is water white and has a consistency of light syrup. This form is preferred as it clings easily to the hair. The Silicone is applied to the entire head, left on for at least ten minutes, and then washed off with any standard shampoo. Within a short time after application of the shampoo, the area is free of any live lice. Any nits do not mature.

Other embodiments include the processing of synthetic lubricants into a shampoo that effectively kills ticks, fleas, and other insects. The concentration of such lubricants, and the amount of time they must remain on the affected area, is above 50% by volume and is adjusted depending on the type of insect being treated. Thus. for example, in two experiments conducted on ticks, the ticks took longer to die than the lice did in the prior experiments using pure Silicone treatment. In the first tick experiment, ten Amblyomma Americanum ticks were coated with Silicone, and ten were coated with Prell® Shampoo. After ten minutes, both sets of ticks were washed with water and Prell® Shampoo for five minutes, until all of the Silicone and shampoo were removed. While all of the "Silicone" ticks were alive after one hour, after six hours three of the ticks were dead, five were morbid, and two were alive. After twenty-four hours, all of the "Silicone" ticks were dead, whereas only two of the "Prell®" ticks were dead.

In a second tick experiment, ten Dermacentor Varibilis ticks were coated with Silicone. After ten minutes all of the ticks were still alive. After ninety minutes, all of the ticks were dead.

While Silicone has been used for many years as a hair-bodying agent, and there are many patents (U.S. Pat. Nos. 3,964,500, 4,427,557, 4,465,619, 4,704,272, 5,728,457, 4,749,732, 4,842,850, 5,015,415, 5,034,218, 5,063,044, 4,902,499, 4,906,459, 5,554,313, 577,644) that focus on using silicone, and some specifically polysiloxanes, for various benefits to the hair. Such use levels have always been at concentrations below 50% wherein effectiveness for insect control was not evident. For actual effectiveness use in the range of 50–100% concentration is required.

It is believed that the lubricating properties of the silicone provide a morbidity passageway for interfering with insect respiratory and possibly digestive functions, and accordingly other similar lubricants and Silicone derivatives are effective in such insect control.

With regard to head lice, the point of entry where the silicone permeates the head lice is very likely the thoracic spiracle, the honeycomb structure which creates maximum surface area and efficient exchange of air and moisture. The nits are likely affected via the head louse nit operculum which contain doughnut shaped holes. See Meinking, T. L. *Current Problems in Dermatology* 11(3) pp 73–120 May/June 1999.

With regard to head lice many natural oils treatments have been attempted but with limited efficacy. In a school based study to evaluate alternative treatments, children with head lice were treated with olive oil, mayonnaise, or Vasoline® petroleum jelly overnight under a shower cap. They came to school the next day with their greasy hair still covered by shower caps. After a shampoo rinse, the lice from heads treated with olive oil or mayonnaise were found to still be alive. The children who used Vasoline® had many dead nymphs stuck to the scalp or hair but some adult lice were still alive. See Meinking , T. L., ibid.

The efficacy of silicone based lubricants over other oils appears to be related to the lubricity of silicone. Silicone and more particularly Dimethylpolysiloxane (or Polydimethylsiloxane) has a far lower surface tension than other oils. Surface tension is a measure of the stretching force required to form a liquid film, and is equal to the surface energy of the liquid per unit length of the film at equilibrium; the force tends to minimize the area of a surface. Surface tension is caused by the attraction of molecules to each other. Below is a list of the surface tension of a variety of polymers and oils at 20° C.

| Polymer/oil system | Surface Tension (dynes/cm) |
|---|---|
| Polydimethylsiloxane (PDMS) | 20.9[1] |
| Polyisobutylene (PIB) | 35.6[1] |
| n-alkanes | 37.8[1] |
| n-fluoroalkanes | 25.9[1] |
| diesel fuel | 25[2] |
| deodorized sunflower oil | 33[2] |
| crude soybean oil | 32[2] |
| refined soybean oil | 32[2] |
| cottonseed oil | 35.4[3] |
| coconut oil | 33.4[3] |
| olive oil | 33.0[3] |
| corn oil | 33.4[4] |
| peanut oil | 35.5[4] |
| mineral oil (MWP paraffin) | 28.8[4] |
| mineral oil-baby oil | 30.8[5] |
| liquid paraffin | 26–28[5] |
| Krytox 1514 | 18[6] |

[1].Ryan, T. W.; Callahan. T. J.; and Dodge, L. G. in Vegetable Oil Fuels, ASAE Conference, 1982 pg. 72
[2].Clarson, S. and Semlyen, J. A. in Siloxane Polymers, PTR Prentice Hall. 1993 pp. 323–325
[3].Encyclopedia of Food Science and Technology, Hui, Y. H. editor Volume 4, pg. 2449 John Wiley and Sons, 1992
[4].Kirk-Othmer Encyclopedia of Chemical Technology, Fourth Edition, Kroschwitz, J. I. and Howe-Grant, M. editors volume 7 pg. 936 John Wiley and Sons, 1992
[5].Internal study by Penrico, courtesy Harold Faust.
[6].Technical data sheet. Dupont.

The surface tension of polydimethylsiloxane at about 20.9 dynes/cm is about 50% lower than the surface tension of most natural oils and is believed to account for its greater ability to penetrate and induce morbidity in insects. In our experiment with Krytox® 1514 a fluorinated oil PerFluoroPolyEther (PFPE), with a surface tension of 18, we found that it was also effective in killing lice but slightly less effective than Dow Coming 200 fluid, 350 CST. The greater effectiveness of the Dow Corning 350 CST material is very likely due to the its greater viscosity. Viscosity, or kinematic viscosity is measured in stokes, and is defined to be the dynamic viscosity divided by the density of the liquid; this gives a quantity which depends only on the type of the liquid, independent of its concentration or density. Krytoxl 514 has a viscosity of 142 centistokes (est). while Dow Corning 200 fluid, 350 CST has a viscosity of 350 cst. The viscosity adds to the effectiveness by creating better adhesion of the lubricant to the insects.

Attempts have been made to modify vegetable oils thru processes such as transesterification in order to lower their surface tensions and thus make them usable as biodiesel fuels. See Cecil, A. W.; Allen, K.; Watts. C. and Ackman R. G. in "Predicting the Surface Tension of Biodiesel Fuels from Their Fatty Acid Composition", *JAOCS* 76(3), pp. 317–323 (March, 1999). It is probable that if vegetable or other oils were processed to lower their surface tension close to the surface tension found in polydimethylsiloxane i.e. less than about 25 dynes/centimeter, it would have the same effect on the lice.

What is claimed is:

1. A method of treating a head lice infestation, in both mature and immature forms, comprising:
   (a) topically applying a composition comprising at least 40% of polydimethylsiloxane by volume to the infestation; and
   (b) allowing the composition to remain on the infestation for at least about five minutes;
   wherein the surface tension of the composition is below about 25 dynes/centimeter at 20° C. and the viscosity of the composition is above about 200 centistokes at 20° C.

2. A method of treating an infestation of nits of head lice, in both mature and immature forms, comprising:
   (a) topically applying a composition comprising at least 40% of polydimethylsiloxane by volume to the infestation; and
   (b) allowing the composition to remain on the infestation for at least about five minutes;
   wherein the surface tension of the composition is below about 25 dynes/centimeter at 20° C. and the viscosity of the composition is above about 200 centistokes at 20° C.

3. A method of treating a head lice infestation, in both mature and immature forms, comprising:
   (a) topically applying a composition comprising at least 50% of polydimethylsiloxane by volume to the infestation; and
   (b) allowing the composition to remain on the infestation for at least about five minutes;
   wherein the surface tension of the composition is below about 25 dynes/centimeter at 20° C. and the viscosity of the composition is above about 200 centistokes at 20° C.

4. A method of treating an infestation of nits of head lice, in both mature and immature forms, comprising:
   (a) topically applying a composition comprising at least 50% of polydimethylsiloxane by volume to the infestation; and
   (b) allowing the composition to remain on the infestation for at least about five minutes;
   wherein the surface tension of the composition is below about 25 dynes/centimeter at 20° C. and the viscosity of the composition is above about 200 centistokes at 20° C.

5. A method of treating a head lice infestation, in both mature and immature forms, comprising:
   (a) topically applying a composition comprising at least 60% of polydimethylsiloxane by volume to the infestation; and
   (b) allowing the composition to remain on the infestation for at least about five minutes;
   wherein the surface tension of the composition is below about 25 dynes/centimeter at 20° C. and the viscosity of the composition is above about 200 centistokes at 20° C.

6. A method of treating an infestation of nits of head lice, in both mature and immature forms, comprising:
   (a) topically applying a composition comprising at least 60% of polydimethylsiloxane by volume to the infestation; and
   (b) allowing the composition to remain on the infestation for at least about five minutes;
   wherein the surface tension of the composition is below about 25 dynes/centimeter at 20° C. and the viscosity of the composition is above about 200 centistokes at 20° C.

* * * * *